(12) United States Patent
Hong et al.

(10) Patent No.: US 11,872,389 B2
(45) Date of Patent: Jan. 16, 2024

(54) STIMULATION APPARATUS AND STIMULATION METHOD USING SAME

(71) Applicant: BARUN GONGHAK CO., LTD., Seoul (KR)

(72) Inventors: Jinkee Hong, Seoul (KR); Sangmin Lee, Gwangmyeong-si (KR)

(73) Assignee: BARUN GONGHAK CO., LTD., Seoul (KR)

( * ) Notice: Subject to any disclaimer, the term of this patent is extended or adjusted under 35 U.S.C. 154(b) by 0 days.

(21) Appl. No.: 17/058,611

(22) PCT Filed: Dec. 13, 2019

(86) PCT No.: PCT/KR2019/017705
§ 371 (c)(1),
(2) Date: Nov. 24, 2020

(87) PCT Pub. No.: WO2020/122668
PCT Pub. Date: Jun. 18, 2020

(65) Prior Publication Data
US 2021/0290944 A1 Sep. 23, 2021

(30) Foreign Application Priority Data

Dec. 13, 2018 (KR) .................. 10-2018-0160915

(51) Int. Cl.
*A61N 1/00* (2006.01)
*A61N 1/04* (2006.01)
*A61N 1/40* (2006.01)

(52) U.S. Cl.
CPC ......... *A61N 1/0468* (2013.01); *A61N 1/0492* (2013.01); *A61N 1/40* (2013.01)

(58) Field of Classification Search
None
See application file for complete search history.

(56) References Cited

U.S. PATENT DOCUMENTS

| | | | |
|---|---|---|---|
| 2014/0190009 A1* | 7/2014 | Anderson | A61N 1/05 29/877 |
| 2016/0156282 A1* | 6/2016 | Kim | A61N 1/0484 607/61 |
| 2019/0381324 A1* | 12/2019 | Wang | A61N 1/36007 |

FOREIGN PATENT DOCUMENTS

| | | |
|---|---|---|
| JP | 2000192301 A | 7/2000 |
| JP | 3163539 U | 10/2010 |

(Continued)

OTHER PUBLICATIONS

Korean Intellectual Property Office, Office Action Issued in Application No. 10-2019-0166416, dated Aug. 17, 2021, 9 pages.

(Continued)

*Primary Examiner* — John R Downey
*Assistant Examiner* — Anant A Gupta
(74) *Attorney, Agent, or Firm* — McCoy Russell LLP

(57) ABSTRACT

The present invention relates to a stimulation apparatus for applying electrical stimulation to a subject for stimulation application. Specifically, a stimulation apparatus according to the present invention comprises: a stimulation part comprising a first conductive member and a first surface which comes into contact with a subject for stimulation application and to which an alternating electric field transmitted from the subject for stimulation application upon contact is input; a conductive part comprising a second conductive member and positioned away from the stimulation part; and a connecting member for electrically connecting the stimulation part and conductive part.

15 Claims, 6 Drawing Sheets

A - A'

(56) References Cited

FOREIGN PATENT DOCUMENTS

| KR | 20120001299 U | 2/2012 |
|---|---|---|
| KR | 101552445 B1 | 9/2015 |
| KR | 20150142810 A | 12/2015 |
| KR | 20160137200 A | 11/2016 |
| KR | 20170094220 A | 8/2017 |
| KR | 20180071132 A | 6/2018 |
| KR | 101875271 B1 | 7/2018 |

OTHER PUBLICATIONS

Korean Intellectual Property Office, Office Action Issued in Application No. 10-2019-0166561, dated Aug. 17, 2021, 11 pages.
Korean Intellectual Property Office, Notice of Allowance Issued in Application No. 10-2019-0166561, dated Feb. 17, 2022, 7 pages.
Kim, T. et al., "Energy-loss return gate via liquid dielectric polarization," Nature Communications, vol. 9, No. 1437, Apr. 12, 2018, 10 pages.
ISA Korean Intellectual Property Office, International Search Report Issued in Application No. PCT/KR2019/017705, dated Aug. 28, 2020, WIPO, 3 pages.

\* cited by examiner

STIMULATION APPARATUS AND STIMULATION METHOD USING SAME

CROSS REFERENCE TO RELATED APPLICATIONS

The present application is a U.S. National Phase of International Application No. PCT/KR2019/017705 entitled "STIMULATION APPARATUS AND STIMULATION METHOD USING SAME," and filed on Dec. 13, 2019. International Application No. PCT/KR2019/017705 claims priority to Korean Patent Application No. 10-2018-0160915 filed on Dec. 13, 2018. The entire contents of each of the above-listed applications are hereby incorporated by reference for all purposes.

TECHNICAL FIELD

The present invention relates to a stimulation apparatus which is not connected with an artificial external power source and may give electrical stimulation to a subject to be stimulated using subtle energy to be wasted, and a stimulation method using the same.

BACKGROUND AND SUMMARY

In the human body, a voltage of −30 to −25 mV is maintained and a weak bioelectricity of about 40 to 60 µA flows while transferring signals between organs. Recently, it has been proved that application of a micro-electrical stimulation having a similar intensity to the bioelectricity (e.g., a current of about 1000 µA or less) has effects such as wrinkle improvement, promotion of wound and fracture healing, improvement of muscle fatigue, inflammation improvement, blood circulation improvement, and abdominal fat reduction.

However, since a conventional micro-electrical stimulation apparatuses should be provided with a separate energy source (power source) for driving a device such as a external power or rechargeable battery or an energy harvester using triboelectrification and are required to be electrically connected to an energy source, it has a complicated configuration and a limitation in miniaturization, has poor portability so that it is difficult to wear (use) the apparatus in everyday life, and has a low energy efficiency due to a dielectric loss or the like described above during operation.

On the other hand, a technology of incorporating a metal for oxidation into a hydrocolloid to produce internal voltage in the hydrocolloid by electrons generated by an oxidation reaction of the metal, as an apparatus to apply an electrical stimulation without being provided with a separate power source, has been suggested, but the hydrocolloid itself has a specific conductivity by moisture, and thus, it is easy for the generated electrons to be lost to the outside, and it is difficult to generate electrons continuously by a metal oxide coat generated by oxidation. In addition, a technology of joining two elements of a metal element and a semiconductor material on an electron conductive medium in contact with skin in a junction to allow a current to flow between the metal element and the semiconductor material through the electron conductive medium as a passage, has been suggested, but it is difficult for an electrical stimulation to be generated after electrical equilibrium between two elements in which contact resistance with the electron conductive medium and a voltage drop by resistance of the electron conductive medium itself are considered by flowing an initial constant current. Thus, like the conventional technologies, when applying a static potential to a wound, only a temporary stimulation is possible, and thus, development of a technology to continuously give an electrical stimulation to a wound is demanded.

DISCLOSURE

Technical Problem

An object of the present invention is to provide a stimulation apparatus which is not required to be connected to an external power source or connected to a rechargeable battery, an energy harvester using triboelectrification, an electrical energy source such as a thermoelectric generation element or a solar cell, and the like, and may constantly apply a micro-electrical stimulation to a subject to be stimulated using energy which is naturally produced and wasted, and a stimulation method.

Technical Solution

In one general aspect, a stimulation apparatus includes: a stimulation part including a first conductive member and a first surface, the first surface being configured to be in contact with a subject to be stimulated and an alternating electric field propagated in the subject to be stimulated being input to the first surface upon contact; a conductive part including a second conductive member and being disposed apart from the stimulation part; and a connection member electrically connecting the stimulation part and the conductive part.

In the stimulation apparatus according to an exemplary embodiment of the present invention, upon contact, potentials different from each other may be formed in the stimulation part and the conductive part by the alternating electric field propagated in the subject to be stimulated.

In the stimulation apparatus according to an exemplary embodiment of the present invention, the alternating electric field may result from triboelectrification.

In the stimulation apparatus according to an exemplary embodiment of the present invention, the subject to be stimulated may be a living body.

In the stimulation apparatus according to an exemplary embodiment of the present invention, upon contact, the first surface is fixed to the subject to be stimulated and a contact area between the stimulation part and the subject to be stimulated may be maintained constant by fixation.

In the stimulation apparatus according to an exemplary embodiment of the present invention, upon contact, a relative position of the conductive part to the stimulation part may be maintained constant.

In the stimulation apparatus according to an exemplary embodiment of the present invention, the conductive part may be disposed apart from the stimulation part in a horizontal or vertical direction to the stimulation part.

In the stimulation apparatus according to an exemplary embodiment of the present invention, the first surface may be provided by a surface of the first conductive member.

In the stimulation apparatus according to an exemplary embodiment of the present invention, the first surface may be configured so that at least a part of the first surface is inserted into the subject to be stimulated.

In the stimulation apparatus according to an exemplary embodiment of the present invention, the conductive part may include the second surface having a greater sheet resistance than the sheet resistance of the first surface.

In the stimulation apparatus according to an exemplary embodiment of the present invention, the second surface may be a surface of an insulator.

In the stimulation apparatus according to an exemplary embodiment of the present invention, the conductive part may be fixed to the subject to be stimulated by the second surface.

In the stimulation apparatus according to an exemplary embodiment of the present invention, the second surface may be provided by a covering material wrapping the second conductive member.

In the stimulation apparatus according to an exemplary embodiment of the present invention, at least, a dielectric disposed in a spacing between the stimulation part and the conductive part may be further included.

In the stimulation apparatus according to an exemplary embodiment of the present invention, the dielectric may fill in an empty space between the stimulation part and the conductive part.

In the stimulation apparatus according to an exemplary embodiment of the present invention, the conductive part may be disposed apart from the stimulation part in a vertical direction to the stimulation part.

In the stimulation apparatus according to an exemplary embodiment of the present invention, one end of the connection member may be in contact with the first conductive member and the other end may be in contact with the second conductive member.

In the stimulation apparatus according to an exemplary embodiment of the present invention, the first conductive member and the second conductive member may be independently of each other a layer, a rod, a plate, a wire, or a combination thereof.

In the stimulation apparatus according to an exemplary embodiment of the present invention, the first conductive member and the second conductive member may be independently of each other a mesh; a perforated film; a network of one or two or more conductive unit bodies selected from fibrous, particulate, tubular, and plate shapes; a shape by continuous arrangement in which basic units adjoin each other, the basic unit being one or more plate shapes selected from a polygon, a circle, and an ellipse of conductive materials In the stimulation apparatus according to an exemplary embodiment of the present invention, the conductive unit body may be dispersed and bound to a non-conductive matrix.

The stimulation apparatus according to an exemplary embodiment of the present invention may further include a protective layer which is configured to cover a surface of the stimulation part, a surface of the conductive part, or surfaces of the stimulation part and the conductive part exposed to the atmosphere upon contact with the subject to be stimulated through the first surface.

In the stimulation apparatus according to an exemplary embodiment of the present invention, N (a natural number of N≥2) stimulation parts and M (a natural number of 1≤M≤N) conductive parts may be included, and N stimulation parts may be connected to M conductive parts by the connection member provided for each stimulation part.

In the stimulation apparatus according to an exemplary embodiment of the present invention, N may be 2 or more, and the stimulation apparatus may further include a second connection member connecting the conductive parts to each other.

In the stimulation apparatus according to an exemplary embodiment of the present invention, the first conductive member and the second conductive member may be independently of each other metals, conductive carbon materials, conductive organic materials, conductive oxides, or combinations thereof.

In another general aspect, a stimulation apparatus includes: a stimulation part including a first conductive member, the first conductive member including a first surface being configured to be in contact with a subject to be stimulated and to which an alternating electric field propagated in the subject to be stimulated is input upon contact; a conductive part including a second conductive member and an insulating covering material wrapping the second conductive member; and a connection member electrically connecting the first conductive member of the stimulation part and the second conductive member of the conductive part.

In another general aspect, a stimulation method using the stimulation apparatus described above is included.

In still another general aspect, a stimulation method includes: fixing a first surface of a stimulation apparatus to a stimulation area of a subject to be stimulated.

Advantageous Effects

The stimulation apparatus according to the present invention does not need an external power source or an artificially manufactured electrical energy generator, and may apply an electrical stimulation to a subject to be stimulated by micro-electrical energy produced by triboelectrification which is inevitably generated in the subject to be stimulated.

In addition, since the stimulation apparatus according to the present invention uses micro-electrical energy propagated from an area where triboelectrification of the subject to be stimulated is generated to the entire area of the subject to be stimulated by dielectric polarization of moisture contained in the subject to be stimulated, or the like, an electrical connection between the area where triboelectrification is generated (an area where micro-electrical energy is produced) in the subject to be stimulated and the stimulation apparatus is unnecessary and substantially no loss of micro-electrical energy produced by triboelectrification occurs, and thus, the stimulation apparatus may have extremely excellent energy efficiency.

In addition, since the stimulation apparatus according to the present invention may continuously apply an electrical stimulation having a similar intensity to bioelectricity, it is effective for recovery of damages such as wounds or fractures, lesion healing such as inflammation improvement, homeostasis improvement such as muscle fatigue improvement or blood circulation improvement, anti-aging such as increased skin elasticity, alleviation of diseases such as obesity, or beauty care.

DETAILED DESCRIPTION

Best Mode

Figure 1:
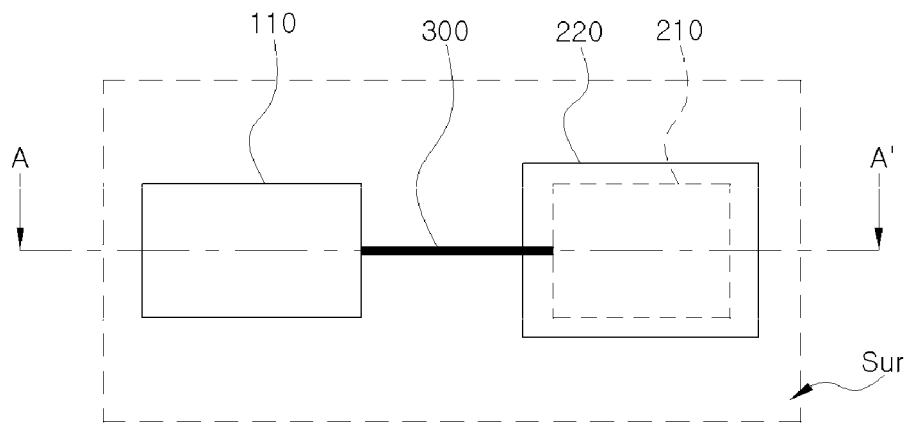
FIG. 1 is a perspective bird's-eye view illustrating a state in which the stimulation apparatus according to an exemplary embodiment is in contact with and fixed to human skin.
Figure 1:
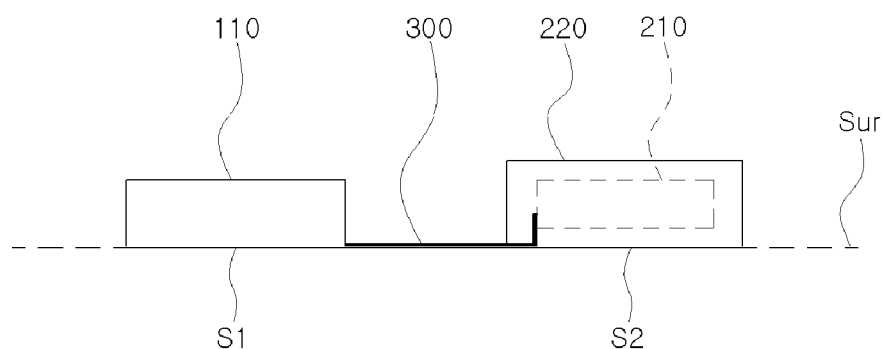

Hereinafter, the stimulation apparatus of the present invention and the stimulation method using the same will be described in detail, with reference to the attached drawings. The drawings to be provided below are provided by way of example so that the idea of the present invention can be sufficiently transferred to a person skilled in the art to which the present invention pertains. Therefore, the present invention is not limited to the drawings provided below but may be embodied in many different forms, and the drawings suggested below may be exaggerated in order to clear the spirit of the present invention. Technical terms and scientific terms used herein have the general meaning understood by those skilled in the art to which the present invention pertains unless otherwise defined, and a description for the known function and configuration which may unnecessarily obscure the gist of the present invention will be omitted in the following description and the accompanying drawings. In addition, the singular form used in the specification and claims appended thereto may be intended to also include a plural form, unless otherwise indicated in the context. In addition, a case in which any one part is connected with another part includes not only a case in which the parts are directly connected with each other but also a case in which the parts are connected with each other with another member interposed therebetween.

The present applicant noted that water is a very effective liquid dielectric and most living bodies contain a large amount of water (70-80% of body weight), and confirmed that a subject containing a large amount of water such as a living body itself may act as a medium capable of transferring (propagating) micro-energy almost without a loss by a dielectric phenomenon.

Meanwhile, the present applicant recognized and noted that a charging phenomenon occurs on the surface of all subjects (objects) substantially present by contact between living body-substance (non-living body, solid/liquid), substance (solid/liquid)-substance (solid/liquid), or living body-living body, and an electrical equilibrium state is changed by contact change which is inevitably accompanied in the process of contact to generate an electric field in an alternating form (a triboelectric effect), as well as confirmed the above.

Thus, an apparatus capable of producing an electrical stimulation using a micro-exogenous alternating electric field which is propagated (transferred) in a subject (including a surface) through micro-exogenous alternating current (exogenous alternating current: based on a triboelectrification generation area, exogenous alternating electric field: based on an area propagated by dielectric polarization) which is inevitably generated in the subject by a triboelectric effect and dielectric polarization by moisture contained in the subject has been developed, thereby completing the present invention.

In the description of the present invention, the contents to be described later may correspond to each embodiment of the present invention.

In one general aspect, a stimulation apparatus includes: a stimulation part including a first conductive member and a first surface, the first surface being configured to be in contact with a subject to be stimulated and an alternating electric field propagated in the subject to be stimulated being input to the first surface upon contact; a conductive part including a second conductive member and being disposed apart from the stimulation part; and a connection member electrically connecting the stimulation part and the conductive part.

The apparatus according to the present invention may apply an electrical stimulation to a subject, by micro-electrical energy by triboelectrification which should essentially occur in the subject. Accordingly, there is no need to use (connect) an external power source, provide and use (connect) a separate artificial energy generator such as a battery, an energy harvester, a thermoelectric generation element, and solar cell, or the like.

In other words, each of the stimulation part and the conductive part in the apparatus according to the present invention is not in a state of being electrically connected to a power source (including an external power source and an electrical energy generator). That is, the stimulation apparatus may not include a separate power source such as an electrical energy generator or a battery inside the apparatus, and also, the stimulation part, the conductive part, and the connection member of the apparatus may not be electrically connected to the power source outside the apparatus.

As described above, the alternating electric field input (applied) to the first surface may be caused by triboelectrification, and specifically, may be caused by triboelectrification (natural triboelectrification) produced by naturally occurring friction on the subject to be stimulated.

In addition, the apparatus according to the present invention may have extremely excellent energy efficiency, since micro-electrical energy (alternating electric field) generated by triboelectrification of a subject is propagated (transferred) by a dielectric polarization phenomenon of a dielectric liquid such as moisture contained in the subject and the micro-electrical energy is supplied therefrom. That is, since the micro-electrical energy generated by triboelectrification is transferred to the apparatus by dielectric polarization of moisture contained in the subject or the like, there may be substantially little energy loss.

As is known, an electric field generated by triboelectrification (naturally occurring triboelectrification) is an alternating electric field and a micro-alternating electric field having an order of about $10^{-6}$ to $10^2$ V, as a specific example, a size in a level of about several μV to hundreds of V, as another specific example, a size in a level of tens of μV to tens of V, and as still another specific example, a size in a level of several mV to several V. Here, it is a well-known fact in the triboelectric field that when friction (change in a friction area) occurs, the alternating electric field is produced, and the alternating electric field is produced continuously or discontinuously/regularly or irregularly depending on the type and the frequency of the friction generated in the subject. As a specific example in which the human body is a subject to be stimulated, a micro-alternating electric field in a level of about 1 to 30 Hz and an order of about $10^{-6}$ to $10^2$ V may be naturally produced. However, as an extreme example, even in the case in which weak triboelectrification occurs only once on the subject, the alternating electric field generated by triboelectrification is applied to the apparatus according to the present invention almost without an energy loss to operate the apparatus, and thus, the present invention is not limited to the frequency or the size of the naturally produced triboelectrification. However, when the frequency of the triboelectrification is increased, the frequency of electrical stimulation generation is increased, which is thus advantageous.

As described above, the alternating electric field generated by naturally occurring triboelectrification in the subject (triboelectrification naturally occurring by the movement of a subject or the like) may be propagated from an area where friction occurs (fraction area) to another area (non-fraction area) in the subject through dielectric polarization by a dielectric liquid such as moisture of the subject or the like.

In terms of producing an alternating electric field by higher energy efficiency and a higher frequency of natural triboelectrification, the subject to be stimulated may propagate micro-electrical energy of the triboelectrification substantially without a loss by a high moisture content, and it is more effective that the subject to be stimulated is an animal including a human who may freely move.

Thus, the subject to be stimulated may be a living body, in particular an animal including a human. When the subject to be stimulated is an animal including a human, an area with which the first surface is in contact in the subject to be stimulated may be skin (including scalp), a mucosa, a tooth, an eye, and the like of an animal including a human, in which the mucosa may include an oral mucosa, a nasal mucosa, a urinary mucosa, a genital mucosa, a digestive tract mucosa, a respiratory mucosa, and the like, but is not limited thereto.

In the subject to be stimulated, the stimulation area which is an area to be stimulated using the apparatus (predetermined area) may be a cell, a tissue, a part of a tissue, an organ, a part of an organ, or the like, and furthermore, the stimulation area may include a damaged or inflamed area of skin, muscle, bones, or the like, a lesion area of a tissue or an organ, and the like.

The tissue may include an epithelial tissue, a connective tissue, a muscle tissue, and/or a nervous tissue, and the like. The epithelial tissue may include a single-layer squamous epithelial tissue such as a peritoneum; a stratified squamous epithelial tissue such as skin, tongue, and esophagus; cubical epithelial tissue such as an ovarian surface, a thyroid glandular epithelium, and a sweat gland; a cylinder epithelial tissue such as a mucosal epithelium, epiglottis, and conjunctiva of stomach or intestines; and/or a transitional epithelial tissue such as vesicoureteral and an inner surface of urethra; and the like. The connective tissue may include an inherent connective tissue (including a loose connective tissue and a dense connective tissue) which fills a gap between a tissue and an organ and connects them to each other; and/or a special connective tissue (including a supporting tissue and a liquid tissue) such as blood, lymph, cartilage, and bones. The muscle tissue may include a voluntary muscle, an involuntary muscle such as a myocardium, a nonstriated muscle such as a blood vessel, a uterus, a bladder, and a piloerector muscle, and the like. The nervous tissue may include a brain (cranial nerves), spinal cord (spinal nerves), peripheral nerves, neuroglia, intrinsic nervous plexus (myenteric plexus, submucosal plexus), and the like. An organ may largely include parenchymatous organs such as the liver, spleen, kidneys, and salivary glands, a hallow organ (tubular organ) such as stomach, intestines, a throat, a bladder, and a uterus, or the like, and the organ may include organ systems, such as, circulatory organs (cardiovascular/lymphatic system), digestive organs (alimentary canals/digestive glands), endocrine organs, immune organs, integumentary organs, lymph organs, locomotive organs, nervous systems, reproductive organs, respiratory organs, skeletal organs, and urinary organs, but is not limited thereto.

Though energy efficiency and a stimulation occurrence frequency of the apparatus may be decreased, a subject other than animals including a human is not necessarily excluded in the present invention, and as the subject to be stimulated, a subject in which an alternating electric field is naturally generated by triboelectrification and alternating electric field caused by triboelectrification may be propagated by dielectric polarization of a dielectric liquid such as moisture, is enough.

In a specific example, the stimulation part may include a first conductive member and a first surface configured to be in contact with a subject to be stimulated. When the stimulation part is in contact with the subject to be stimulated through the first surface, an alternating electric field propagated in the subject to be stimulated, specifically, an alternating electric field caused by triboelectrification of the subject to be stimulated, and more specifically, an alternating electric field produced from the triboelectrification of the subject to be stimulated and propagated in the subject to be stimulated by dielectric polarization of moisture of the subject to be stimulated may be input through the first surface (applied to the first surface).

The first surface may be a surface electrically connected to the first conductive member, and the electrical connection may include direct connection or indirect connection. That is, the alternating electric field input through the first surface may be transferred from the first surface to the first conductive member directly (by direct connection) or indirectly (by indirect connection) to form a potential on the first conductive member. Here, the direct connection may mean a case in which the first surface is provided by a conductive member, that is, a case in which the first surface is the (part of the) surface of the first conductive member, and the indirect connection may mean a case in which the alternating electric field is transferred (applied) to the first conductive member through a member providing the first surface (hereinafter, referred to as a contact member).

In a specific example, when the contact member provides the first surface, a contact member which may transfer the alternating electric field input through the first surface to the first conductive member is enough as the contact member. As an example, the contact member may be disposed in contact with the first conductive member. Here, for the contact member, the position of the first surface is set as a lower portion and an opposite surface side of the first surface is set as an upper portion, so that the first conductive member may be disposed to be in contact with the contact member on the upper portion of the contact member.

As the contact member, a contact member which may receive the alternating electric field through the first surface and transfer (apply) the alternating electric field to the first conductive member is enough. However, the contact member may be substantially conductive, so that the potential of the possible input alternating electric field may be applied to the first conductive member without a loss of the potential. As an example of the conductive contact member, the contact member may be a metal, a conductive carbon materials, a conductive organic material, a conductive oxide, or a combination thereof, which is different from the first conductive member. Here, specific materials of the metal, the conductive carbon material, the conductive organic material, the conductive oxide, or the combination thereof may be similar or identical to the description below related to the first conductive member.

In a specific example, the first surface may be provided by the first conductive member. That is, the first surface may be a surface of the first conductive member. In this case, the stimulation part includes the first conductive member, but the first conductive member may be configured to be in contact with the subject to be stimulated and may include the first surface to which the alternating electric field propagated in the subject to be stimulated is input upon contact.

In the stimulation apparatus according to a specific example, potentials different from each other may be formed in the stimulation part and the conductive part by the alternating electric field input through the first surface, that is, by the alternating electric field propagated in the subject to be stimulated and input through the first surface, upon contact between the stimulation part and the subject to be stimulated through the first surface. Specifically, upon contact, potentials different from each other may be formed in the first conductive member of the stimulation part and the second conductive member of the conductive part by the alternating electric field propagated in the subject to be stimulated, thereby generating a potential difference between the first conductive member and the second conductive member. By the potential difference, a current in an alternating form is generated between the stimulation part (first conductive member) and the conductive part (second conductive member) and an electrical stimulation may be given to the subject to be stimulated.

Here, since the alternating electric field is moved and propagated by dielectric polarization by moisture in the subject to be stimulated, inputting the alternating electric field to the first surface may mean forming a potential on the first surface in a direction of offsetting the alternating electric field (neutralizing charges in the contact area between the subject to be stimulated and the first surface) by the dielectric polarization.

Without being necessarily limited to the interpretation, when the first surface is provided by the first conductive member or the conductive contact member, the first surface is in contact with the alternating electric field moved by the dielectric polarization, thereby forming (charging) complementary charges which may offset the dielectric polarization on the first surface. The conductive part which is electrically connected to the stimulation part by the connection member, specifically the second conductive member which is electrically connected to the stimulation part acts as a pool of free charges (free electrons) similar to a ground, thereby supplying the complementary charges from the second conductive member. Thus, a potential difference may be formed between the stimulation part (specifically, the first conductive member) and the conductive part (specifically, the second conductive member). In terms of the motion mechanism, the second conductive member of the conductive part may be referred to as a free charge source.

By the potential difference between the stimulation part (specifically, first conductive member) and the conductive part (specifically, second conductive member) caused by the alternating electric field, a current in an alternating form is generated between the stimulation part and the conductive part and an electrical stimulation may be given to the subject to be stimulated. Here, the electrical stimulation applied to the subject to be stimulated may be a current stimulation, a stimulation applied by an electric potential, or a stimulation by both the current and the potential. In an exemplary embodiment, the electrical stimulation may be a stimulation by an electrical potential.

As long as the conductive part is electrically connected to the stimulation part through the connection member and apart from the stimulation part (as long as substantially the second conductive member of the conductive part is electrically connected to the first conductive member of the stimulation part through the connection member and the second conductive member and the first conductive member are not physically in contact with each other), the apparatus is not significantly affected by the position of the conductive part relative to the stimulation part.

Thus, an in-plane direction of the first surface is set as a horizontal direction and a direction vertical to the first surface (out-of plane) is set as a vertical direction, so that the conductive part (specifically the second conductive member of the conductive part) may be disposed apart from the stimulation part in any direction such as a horizontal or vertical direction to the stimulation part.

The conductive part may include a second surface having a higher sheet resistance than the sheet resistance of the first surface. Specifically, a ratio of sheet resistance of the second surface/sheet resistance of the first surface may be an order of $10_1$ or more, specifically an order of $10^2$ or more, and more specifically an order of $^{103}$ or more. As a substantial example, the second surface may be an insulating surface and the first surface may be a conductive surface.

According to an exemplary embodiment, the conductive part may include the second conductive member and an insulator providing the second surface. The insulator may have a structure of being laminated on the second conductive member or wrapping the second conductive member. When the insulator is laminated on the second conductive member, the insulator is laminated on a position in which the second conductive member and the first conductive member may be prevented from being in direct contact with each other, and/or a position in which the second conductive member is prevented from being in direct contact with the subject to be stimulated.

As a substantial example, the conductive part may include the second conductive member and an insulating covering material (insulator) wrapping the second conductive member, and the second surface may be a surface of the insulating covering material. The insulating covering material may include an insulating organic material, an insulating inorganic material, or a composite thereof. The insulating inorganic material may be metals (including transition metals, post-transition metals, alkali metals, and alkaline earth metals), or oxides, nitrides, carbides, oxynitrides, and carbonitrides of metalloids, and the like, and the insulating organic material may be insulating resins. The insulating resin may be synthetic resins, natural polymers, biocompatible polymers, or mixtures thereof, and the like. The synthetic resin may include thermocurable resins (including thermocurable elastomers), thermoplastic resins (including thermoplastic elastomers), or mixed resins thereof, and the like. The thermoplastic resin may include ethylene-based resins, propylene-based resins, styrene-based resins, methacryl-based resins, vinyl alcohol-based resins, vinyl chloride-based resins, olefin-based resins, ester-based resins, amide-based resins, urethane-based resins, carbonate-based resins, mixtures thereof or composites thereof, and the like. The thermocurable resin may include phenol-based resins, urea-based resins, melamine-based resins, unsaturated ester-based resins, epoxy-based resins, silicone-based resins, fluorine-based resins, phthalate-based resins, mixtures thereof or composite resins thereof, and the like. As a specific example of the synthetic resin, a polymethylmethacrylate (PMMA) resin, a polyethylene terephthalate (PET) resin, a polyethylene (PE) resin, a low-density polyethylene (LDPE) resin, a linear low-density polyethylene (LLDPE) resin, a polypropylene (PP) resin, a polystyrene (PS) resin, a polyisoprene resin, an ethylene vinyl acetate resin(EVA) resin, a polyethylene carbonate resin, a polypropylene polycarbonate resin, a phenol-formaldehyde resin, a polyethylene terephthalate (PET) resin, a polyethylene naphthalate (PEN) resin, a polyimide (PI) resin, a polycarbonate (PC) resin, a triacetyl cellulose (TAC), a polyether sulfone (PES) resin, a nylon resin, a styrene butadiene rubber (SBR), an isoprene rubber (IR), a butadiene rubber (BR), an ethylene propylene rubber (EPM), an ethylene propylene diene rubber (EPDM), an acrylate rubber (ACM), an ethylene acrylate rubber (AEM), an acrylonitrile butadiene rubber (NBR), a hydrogenated acrylonitrile butadiene rubber (HNBR), a chloroprene rubber (CR), chlorosulfonated polyethylene (CSM), an ethylene vinyl acetate rubber (EVM), a silicone rubber (VSI), or mixtures thereof or composite resins thereof may be included, but the present invention is not limited thereto. A natural polymer may be proteins, carbohydrates, starches, natural rubber (including cis-1,4-polyisoprene as a main body), and the like having a molecular weight of 1000 or more, and specifically, may be gelatin, collagen, hyaluronic acid, glycosaminoglycan, sodium alginate, alginate, hyaluronan, agarose, polyhydroxy butylate, fibrin, gluten, albumin, elastin, cellulose, starch, or mixtures thereof, and the like, but is not limited thereto. The biocompatible polymer may include biodegradable polymers, biosoluble polymers, or mixtures thereof, and the biodegradable polymer may be poly(lactide), poly(glycolide), poly(lactide-co-glycolide), polyanhydride, polyorthoester, polyetherester, polycaprolactone, polyesteramide, poly(butyric acid), poly(valeric acid), polyurethane, copolymers thereof or mixtures thereof, and the like, but is not limited thereto. The biosoluble polymer may be gelatin, pectin, dextran, hyaluronic acid or salts thereof, collagen, agar, arabic gum, xanthan gum, acacia gum, karaya gum, tragacanth gum, guar gum, carrageenan acid, alginic acid, alginic salts (e.g., sodium alginate), methyl cellulose, ethyl cellulose, hydroxyethyl cellulose, sodium carboxymethyl cellulose, soluble starch, pullulan, dextrin, carboxymethyl starch, dialdehyde starch, polyvinyl alcohol, polyvinyl pyrrolidone, polyvinyl methacrylate, polyacrylic acid and salts thereof, polyethylene oxide, polypropylene oxide, a copolymer of polyethylene oxide and polypropylene oxide, a carboxyl group-containing acryl resin, a carboxyl group-containing polyester resin, water-soluble polyamide, water-soluble polyurethane, maltodextrin, polydextrose, or mixtures thereof, and the like, but is not limited thereto.

However, as described above, it should not be limited to and construed as being the second surface being provided by the insulator. It is because even when both the first surface and the second surface are in contact with the subject to be stimulated, in the case in which the sheet resistance of the second surface is higher than the sheet resistance of the first surface, a potential difference between the conductive part and the stimulation part may be formed.

Thus, an example in which the second surface is provided by an insulator is only an advantageous example in which even when both the first surface and the second surface are in contact with the subject to be stimulated, a large potential difference between the conductive part and the stimulation part may be resulted. As long as the spirit of the present invention is implemented, a case in which the second surface is provided by a conductor having a higher sheet resistance than the sheet resistance of the first surface or a semiconductor is not completely excluded from the present invention.

That is, the conductive part may include a high-impedance member having the second surface having a higher sheet resistance than the sheet resistance of the first surface, and the high-impedance member may include an insulator, a semiconductor, a conductor, or a mixture thereof. Here, as described above, the high-impedance member may have a ratio of the sheet resistance of a member surface divided by the sheet resistance of the first surface of an order of $10^1$ or more, specifically an order of $10^2$ or more, and more specifically an order of $10^3$ or more. As an example, a network of a conductive nanostructure having a high sheet resistance relative to a metal film by a contact resistance, a composite in which the conductive nanostructure and the insulator are composited, or the like may belong to the high-impedance member. Here, the conductive nanostructure may include a conductive nanofiber or a conductive nanowire, a conductive nanoplate, conductive nanoparticles, or a mixture thereof, but is not necessarily limited thereto. In addition, when the high-impedance member contains the conductive nanostructure, in terms of forming a high sheet resistance, the conductive nanostructure may be contained at a limiting concentration or lower of substantially not forming a continuous current moving path. However, a higher sheet resistance than the sheet resistance of the first surface is enough, and the concentration of the conductive nanostructure contained in the high-impedance member is not necessarily limited to the limiting concentration or lower.

In addition, when the high-impedance member is an insulator and the second conductive member is coated with the high-impedance member, the high-impedance member may correspond to the insulating covering material described above.

Similarly to the case of the insulator, when the conductive part includes the high-impedance member providing the second surface, the high-impedance member may be laminated on a position in which the second conductive member and the first conductive member may be prevented from being in direct contact with each other, may be laminated on a position in which the second conductive member may be prevented from being direct contact with the subject to be stimulated, and/or may wrap the second conductive member.

As a specific example, the conductive part may also be in contact with the subject to be stimulated, like the stimulation part. In this case, the conductive part may include the second surface. Specifically, the conductive part may be disposed apart from the stimulation part in a horizontal direction to the stimulation part, and when the first surface is in contact with the subject to be stimulated, the conductive part may also be in contact with the subject to be stimulated through the second surface. The second surface may prevent a direct contact between the second conductive member of the conductive part and the subject to be stimulated and may prevent the same potential as the potential to the first conductive member from being applied to the second conductive member.

Thus, in an exemplary embodiment, the conductive part is disposed apart from the stimulation part in a horizontal direction to the stimulation part, and may have the second conductive member and the second surface which has a higher sheet resistance than the sheet resistance of the first surface and is insulating according to an advantageous example. In addition, when being in contact with the subject to be stimulated, the stimulation part may be fixed to the subject to be stimulated through the first surface, and the conductive part may be fixed to the subject to be stimulated through the second surface.

FIG. 1 is an example of a perspective bird's-eye view illustrating a state in which the stimulation apparatus according to an exemplary embodiment is in contact with and fixed to human skin, and illustrated an example in which the subject to be stimulated is the human body, an example in which the conductive part is in contact with the human body like the stimulation part, and an example in which the conductive part is provided with the second insulating surface.

Specifically, the stimulation apparatus according to an exemplary embodiment may be in contact with and fixed to the human body (Sur). The stimulation apparatus may include a stimulation part including a first conductive member 110 providing a first surface S1 which is in contact with and fixed to the human body, a conductive part being disposed apart from the stimulation part and including a second conductive member 210 and an insulating covering material 220 which wraps the second conductive member 210 and provides the second surface S2 which is in contact with and fixed to the human body, and a connection member 300 electrically connecting the first conductive member 110 and the second conductive member 210.

However, in a state before contact, even in the case in which the conductive part is disposed horizontally apart from the stimulation part, when the stimulation part is in contact with the subject to be stimulated, the conductive part is not necessarily in contact with the subject to be stimulated.

Figure 2:
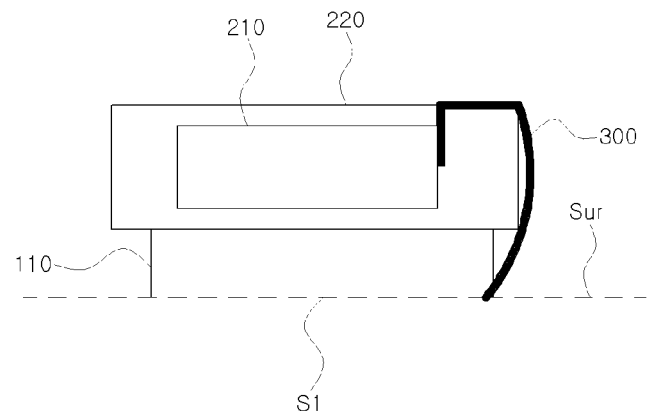
FIG. 2 is a cross-sectional view illustrating a state in which the stimulation apparatus according to an exemplary embodiment is in contact with and fixed to human skin.

As in the example of the cross-sectional view illustrated in FIG. 2, when the connection member 300 has flexibility like wires and the like, even in the case in which the stimulation part and the conductive part are disposed horizontally apart from each other in a state of being not in contact with the human body, the stimulation part may be in contact with and fixed to the human body (Sur) through the first surface S1 and the conductive part may be fixed to and disposed on an upper portion of the stimulation part.

Thus, the stimulation apparatus includes: a stimulation part including a first conductive member and a first surface, the first surface being configured to be in contact with a subject to be stimulated and an alternating electric field propagated in the subject to be stimulated being input to the first surface upon contact; a conductive part including a second conductive member and being disposed apart from the stimulation part; and a connection member electrically connecting the stimulation part and the conductive part, based on a non-contact state with the subject to be stimulated, that is, based on an unused state in which the stimulation apparatus is not used. However, the stimulation apparatus may include: a stimulation part including a first conductive member and a first surface, the first surface being configured to be in contact with a subject to be stimulated and an alternating electric field propagated in the subject to be stimulated being input to the first surface upon contact; a conductive part including a second conductive member being disposed apart from the first conductive member of the stimulation part; and a connection member electrically connecting the stimulation part and the conductive part, based on a non-contact state with the subject to be stimulated, that is, based on a used state in which the stimulation apparatus is used.

As described above through an example of FIGS. 1 and 2, the stimulation part may be configured to be in contact with the subject to be stimulated through the first surface, but fixed to the subject to be stimulated. That is, the stimulation part may be in contact with and fixed to the subject to be stimulated, and the first surface is a surface which may be in contact with and fixed to the subject to be stimulated. By fixation of the first surface, when the stimulation part is contact with the subject to be stimulated, a contact area between the stimulation part and the subject to be stimulated may be maintained constant. That is, the first surface is in contact with and fixed to the subject to be stimulated, thereby maintaining the contact area of the stimulation part with the subject to be stimulated constant.

In addition, at least when the stimulation part and the subject to be stimulated are in contact with each other, a relative position of the conductive part to the stimulation part, specifically, a relative position between the first conductive member and the second conductive member may be maintained constant. The relative position of the conductive part to the stimulation part being maintained constant may mean that the conductive part is fixed to the subject to be stimulated, the conductive part is fixed to the stimulation part similarly to FIG. 2, or the conductive part is fixed to the subject to be stimulated by a separate member provided in advance, at least when the stimulation part and the subject to be stimulated are in contact with each other. For example, when the subject to be stimulated is the human body, the separate member provided in advance in the subject to be stimulated may be daily necessities such as clothing, accessories, glasses, and contact lenses worn on the human body, medical supplies such as braces (teeth, spine, pelvis, and the like), splints, plaster, bandages, gauze, and bands installed or fixed on the human body for treatment, or the like, but the separate member to which the conductive part may be fixed and which is provided in advance on the subject to be stimulated is not limited thereto. Here, in the conductive part being fixed to the separate member provided in advance in the subject to be stimulated, fixation means that there is no intentional change in a position (movement) for causing a certain effect or an act. Thus, it is also included in the category of the fixation that the separate member itself provided in advance in the subject to be stimulated is moved by inevitable movement of the subject to be stimulated or the like to slightly change a separate distance between the conductive part and the stimulation part. Substantially, the separate distance or a change in the separate distance between the conductive part and the stimulation part does not significantly affect the action of the apparatus.

In a specific example, the first surface being configured to be in contact with the subject to be stimulated may mean that the first surface has a shape to be in close contact with the stimulation area (an area to be stimulated) of the subject to be stimulated. Otherwise, the first surface being configured to be in contact with the subject to be stimulated may mean that the first surface has appropriate flexibility or stretchability (or elasticity), so that the first surface may be in close contact with the stimulation area substantially regardless of the shape of the stimulation area. In terms of easily securing flexibility or stretchability (or elasticity) required for the stimulation area which is large and severely curved (as an example, face), the first surface may be provided by a flexible first conductive member, and the flexible first conductive member may include a conductive network or a conductive polymer described later, but is not necessarily limited thereto.

In a specific example, when the first surface and the subject to be stimulated are in contact with each other, the first surface may be in contact with and fixed to the subject to be stimulated, and the second surface may be in contact with and fixed to the subject to be stimulated, the stimulation part, or the separate member provided in advance in the subject to be stimulated. The fixation (fixation of the first surface or the first surface and the second surface) may be assisted by an adhesive member having an adhesive surface (the first surface or the second surface) or at least one adhesive surface.

When the fixation is performed by the adhesive member, the stimulation apparatus according to an exemplary embodiment of the present invention may further include a first adhesive member which may fix the first surface of the stimulation part to the subject to be stimulated upon contact. In addition, if necessary, the stimulation apparatus may further include a second adhesive member which may fix the second surface of the conductive part to the subject to be stimulated or the separate member (other than the subject to be stimulated) provided in advance in the subject to be stimulated. As an example of the adhesive member (the first or second adhesive member), a common adhesive tape including an adhesive layer and a substrate layer, or the like may be included, but the present invention is not limited thereto.

When the first surface or each of the first surface and the second surface has adhesion, the first surface may be a surface having conductivity and adhesion, and the second surface may be a surface having an electrical property of a sheet resistance higher than the sheet resistance of the first surface and adhesion.

As a specific example, the first surface having conductivity and adhesion may be a surface of a conductive material having adhesion. As an example of the conductive material having adhesion, a conductive polymer having adhesion or a mixture of a conductive polymer and an adhesive material (adhesive resin) may be included, but the present invention is not limited thereto.

As a specific example, the first surface having conductivity and adhesion may include an adhesive area where the adhesive material is exposed to the surface and a conductive area where the conductive material is exposed to the surface. As an example, the first surface may include the conductive area and the adhesive area which is positioned on the edge of the conductive area to warp the conductive area, and unlike this, the conductive area and the adhesive area may be regularly or irregularly mixed. When in the first surface, the conductive area and the adhesive area are mixed, the mixed area ratio or the mixed pattern may be such that an alternating electric field is well input and stable adhesion is achieved, and a specific mixed pattern, a specific area ratio, or the like may correspond to a simple modification level of a design by a person skilled in the art considering a specific material, a size, a shape, or the like of the stimulation part.

In addition, when the first surface includes both the conductive area and the adhesive area, the conductive area and the adhesive area may be positioned on the same plane or there may be a fine step between the conductive area and the adhesive area. When the first surface may be somewhat deformed or flexible, the conductive area may be in close contact with the subject to be stimulated even with the fine step between the adhesive area and the conductive area. Presence or absence of the fine step, the mechanical physical properties of a member providing the first surface, or the like belongs to a simple modification example based on the present invention.

The conductive area may be provided by the conductive material, and the adhesive area may be, when weak pressure is applied, bonded to an adherend with a constant bonding force by a covalent bond, an intermolecular force, a van der Waals force, and/or a London's dispersion force, or the like, but may be provided by the adhesive material which is a peelable material. The adhesive material may be a material which has been conventionally commonly used for adhering an adherend to the animal skin including the human body. However, when the subject to be stimulated is the human body, the adhesive material may be an adhesive material with proven biostability, for firmer use stability. As an example of the adhesive material with proven biostability, a copolymer of a carboxyl group or a hydroxyl group-containing monomer and (meth)acrylic ester, a copolymer of a monomer having a nitrogen atom having no salt structure in a side chain and (meth)acrylic ester, a copolymer of a methacryl-based polymer or a vinyl acetate-based polymer and perfluoroalkyl acrylate ester, a copolymer containing 2-acetacetoxyethyl ester methacrylate, an acryl-based pressure-sensitive adhesive having (meth)acrylic acid alkyl ester as a main body constituent monomer, and the like may be included, but the present invention is not limited to the specific kinds of the adhesive material.

In a specific example, the second surface having an electrical property of a sheet resistance higher than the sheet resistance of the first surface and adhesion may include both a high-impedance area where the material of the high-impedance member described above is exposed to the surface and an adhesive area where the adhesive material is exposed to the surface, or since the adhesive material is usually insulating, the second surface itself may be a surface of the adhesive material. When the second surface itself is a surface of the adhesive material, the high-impedance member described above may include a film of the adhesive material which may be at least positioned between the second conductive member and the stimulation area of the subject to be stimulated. When the second surface includes both the high-impedance area and the adhesive area, the second surface may include the high-impedance area and the adhesive area which is positioned on the edge of the high-impedance area to wrap the high-impedance area, and unlike this, the high-impedance area and the adhesive area may be regularly or irregularly mixed. The adhesive material providing the adhesive area on the second surface may be similar or identical to that described above for the first surface.

In a specific example, the first surface may be configured so that at least a part of the first surface is inserted into the subject to be stimulated. That is, the first surface may include an inserted area protruded to be inserted into the subject to be stimulated. Here, each of the non-inserted area (an area in contact with an outer surface of the subject to be stimulated) and the inserted area may be the conductive surface, and unlike this, the non-inserted area may be the conductive surface having adhesion and the inserted area may be the conductive surface. Otherwise, unlike this, the non-inserted area may be the adhesive surface and the inserted area may be the conductive surface. In addition, regardless of whether the surface includes the adhesive area, the stimulation part may be fixed alone or additionally to the subject to be stimulated by the inserted area. In addition, the inserted area may increase a contact area between the subject to be stimulated and the stimulation part.

A protruding shape of the inserted area may be any shape which may be inserted into the subject to be stimulated. As an example, the protruding shape of the inserted area may be a conical shape, an angular conical shape (including a pyramidal shape), a needle shape, or the like, but is not necessarily limited thereto. As an example in which the subject to be stimulated is the human body, the inserted area may be provided by a microneedle formed on a first surface side of the stimulation part, but the present invention is not limited thereto.

A case in which the first surface is provided by the first conductive member is an example, and the first conductive member may include a protruding portion positioned on the first surface in contact with the subject to be stimulated upon contact, and the surface of the protruding portion may correspond to the inserted area. The protruding portion may have a shape of a conical shape, an angular conical shape (including a pyramidal shape), a needle shape, or the like, but is not necessarily limited thereto.

Figure 3:
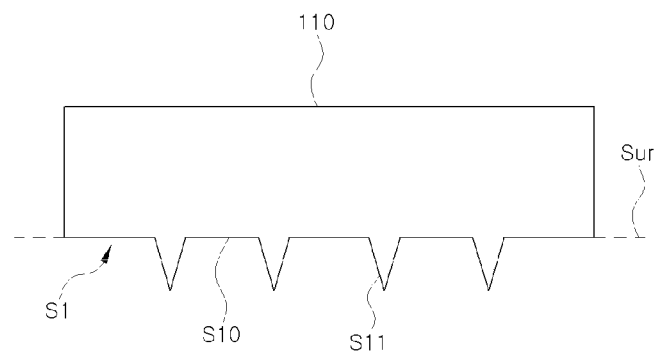
FIG. 3 is a cross-sectional view illustrating only a state in which a stimulation part in the stimulation apparatus according to an exemplary embodiment is in contact with and fixed to human skin.

FIG. 3 is a cross-sectional view illustrating only a state in which in the stimulation apparatus according to an exemplary embodiment, the stimulation part 110 is in contact with and fixed to human skin and is an example in which the subject to be stimulated is the human body, and illustrates an example in which the first surface S1 of the stimulation part 110 includes the non-inserted area S1 and the inserted area S2 by the microneedle and the inserted area S2 provided by the microneedle is inserted and fixed to the human body.

FIG. 1 is a drawing illustrating an example in which the conductive part and the stimulation part are horizontally spaced apart. However, as described above, as long as the second conductive member of the conductive part and the first conductive member of the stimulation part are disposed apart without being in contact with each other, the present invention is not limited to a specific separation distance and a specific separation direction.

Figure 4:
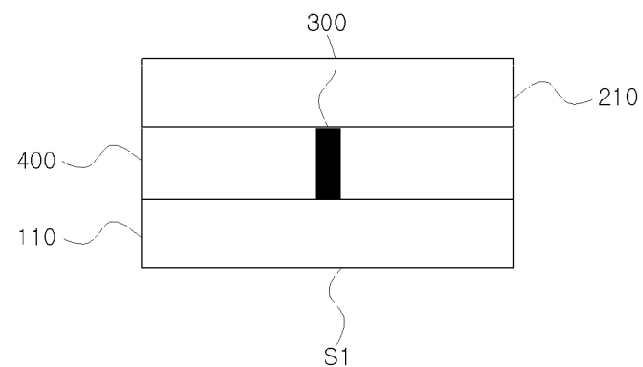
FIG. 4 is a cross-sectional view illustrating a cross section of the stimulation apparatus according to an exemplary embodiment.

As an example, the cross-sectional view of FIG. 4 is a drawing illustrating an example in which the second conductive member 210 of the conductive part and the first conductive member 110 of the stimulation part are disposed apart in a vertical direction to each other. A spacing may be defined by two surfaces facing each other of the second conductive member 210 and the first conductive member 110 and the separation distance therebetween. A connection member 300 is disposed inside the spacing as in an example of FIG. 4 or disposed in a boundary of the spacing or outside the spacing unlike an example of FIG. 4, so that the second conductive member 210 and the first conductive member 110 may be electrically connected. As in an example of FIG. 4, the stimulation apparatus may further include a dielectric 400 disposed in the spacing between the stimulation part and the conductive part, and the spacing may be filled with the dielectric 400.

As described above, the stimulation apparatus may further include the dielectric disposed at least in the spacing between the conductive part and the stimulation part. The dielectric may have a dielectric constant (at 25°) of 1.2 to 3000, 1.5 to 100, 1.2 to 3, 2 to 10, 3 to 150, 3 to 60, 300 to 3000, 500 to 2000, or 500 to 1500. As a specific dielectric material, organic materials such as insulating polymers, insulating ceramics such as oxides, nitrides, carbides, or oxynitrides of one or two or more elements selected from transition metals, post-transition metals, and non-metals, or ferroelectrics having a perovskite structure (as an example, $BaTiO_3$ or the like), organic/inorganic hybrid materials such as polysilsesquioxane or polysiloxane, amorphous materials such as amorphous carbon fluoride or glass, and the like may be included, but the present invention is not limited to the specific dielectric constant of the materials of the dielectric.

In a specific example, one end of the connection member may adjoin the first conductive member and the other end of the connection member may adjoin the second conductive member. The connection member may be only a member which is commonly used for electrically connecting two independent elements.

Specifically, the connection member may include a conductive core and an insulating coating layer which wraps or covers the conductive core so that the conductive core is not exposed to the surface (in the atmosphere). Here, both ends of the conductive core may be bonded to (including binding) the first conductive member and the second conductive member. As an example of the connection member, a core-sheath structure of a conductive wire and an insulating coating layer wrapping the conductive wire, or the like may be included. As a common example of the connection member having the core-sheath structure, a wire may be included, but the present invention is not limited thereto.

As another example, the connection member may be a conductive adhesive including a conductive filler and a curable resin, or the like, but the present invention is not limited to the specific kind of the connection member. However, when the connection member is a conductive adhesive, electric connection by the conductive filler and physical binding by the curable resin may be achieved at the same time.

Figure 5:
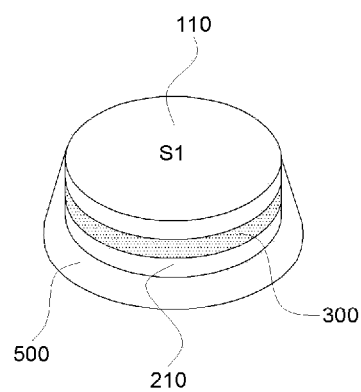
FIG. 5 is a perspective view illustrating the stimulation apparatus according to an exemplary embodiment.

An example of FIG. 5 illustrates an example in which a conductive adhesive layer is used as the connection member 300, and is a drawing illustrating an example in which the second conductive member 210 and the first conductive member 110 are electrically connected by the connection member 300 which is the conductive adhesive layer and physically integrated. As in the example of FIG. 5, in the stimulation apparatus, the first conductive member 110 in the form of a circular plate—the connection member 300 which is the conductive adhesive layer—the second conductive member 210 in the form of a circular plate may be physically integrated, and the stimulation apparatus may be wrapped by a protective layer 500 except a surface (first surface) S1 through which the first conductive member 110 is in contact with skin.

An example of FIG. 5 corresponds to an example in which the first conductive member and the second conductive member have the same shape, the second conductive member and the first conductive member are integrally bound to each other by the conductive adhesive, the conductive adhesive fills the entire spacing where the first conductive member and the second conductive member are separated, and the first conductive member and the second conductive member correspond to each other one-to-one. However, it corresponds to simple modification of the example according to FIG. 5 based on the spirit of the present invention that the conductive adhesive partially fills the spacing where the first conductive member and the second conductive member are separated and electrically connects and integrates the two members, the first conductive member and the second conductive member are connected by the connection member in the form of a wire instead of the conductive adhesive, the members are connected (or attached) many (first conductive member) to one (second conductive member), not one to one correspondence, or the first conductive member and the second conductive member have different forms from each other or the first conductive member and the second conductive member have shapes corresponding to each other but have shapes such as a non-circular oval shape, a polygonal shape such as triangular or octagonal shape, a strip or mesh shape, and a conductive network shape.

When the conductive adhesive is used as the connection member, the conductive adhesive may be any conductive adhesive which is commonly used in the fields of package or chip mounting, and as an example, the conductive filler may be particles of silver, gold, copper, nickel, carbon, or metal-coated polymers, intrinsically conductive polymers, or the like, and the curable resin may be any resin having a curable functional group, which is cured by a chemical material such as a curing agent, or heat and/or light. As an example of the curable resin having high flexibility and elasticity, a siloxane-based resin, an olefin-based elastic resin, a polyurethane-based resin, or the like may be included, but the present invention is not limited thereto.

In addition, the first conductive member and the second conductive member may be commonly called a first electrode and a second electrode, and between the first conductive member and the second conductive member, a resistance by the connection member connecting the two members, as an example, a contact resistance generated in a joining area between the electrode (first conductive member or second conductive member) and the connection member, a resistance of the connection member itself, or the like may be formed. The resistance between the first conductive member and the second conductive member may be in a range of an order of $10^{-1}$ Ω/cm to an order of $10^6$ Ω/cm, but is not limited thereto. However, the resistance (impedance) provided by the connection member may be higher than the resistance of each of the first conductive member and the second conductive member.

In a specific example, the first conductive member and the second conductive member may independently of each other contain a conductive material, and the conductive material may include metals, conductive carbon materials, conductive organic materials, conductive oxides, or combinations thereof. Here, the combination may also include composite materials such as a metal with a conductive carbon material, a conductive organic material with a conductive carbon material, and a metal with a conductive organic material. In an exemplary embodiment, the first conductive member and the second conductive member may be the same conductive material, but may be different conductive materials from each other. As an example, the first conductive member and the second conductive member may be the same metal.

As a specific example, the conductive carbon material may include carbon fibers, activated carbons, carbon nanotubes, graphite, carbon black, graphene (reduced graphene oxide), combinations thereof, but is not limited thereto.

The conductive organic material may include conductive polymers. As an example, the conductive polymer may be any one or two or more selected from polyacetylene-based, polyaniline-based, polypyrrole-based, polythiophene-based polymers, and the like, but is not limited thereto. As a substantial example, the conductive polymer may be any one or two or more selected from polyacetylene (PA), polyaniline (PANI), polypyrrole (PPy), polythiophene (PT), poly(3,4-ethylenedioxythiophene) (PEDOT), polyisothianaphthene (PITN), polyphenylene vinylene (PPV), polyphenylene (PPE), polyphenylene sulfide (PPS), polysulfur nitride (PSN), and the like, but is not limited thereto.

Since the metal is a very good conductor itself, the metal may be one or more metals or alloys thereof selected from alkali metals, alkaline earth metals, transition metals, and post-transition metals, and the like. However, when the first conductive member provides the first surface, for firmer use stability than the case in which the subject to be stimulated is a human, the metal of the first conductive member may be a metal of which the biostability upon contact has been confirmed, such as copper, gold, silver, stainless steel, and aluminum, but is not necessarily limited thereto.

The conductive oxide may be a transparent conductive oxide which is commonly used as a transparent electrode, and the transparent conductive oxide may include fluorine doped tin oxide (FTO), Indium doped tin oxide (no), Ga doped ZnO (GZO), Al doped ZnO (AZO), ZnO, $SnO_2$, $TiO_2$, and the like, but is not limited thereto.

In a specific example, the first conductive member and the second conductive member may be independently of each other in the form of a layer, a rod, a plate, a wire of conductive materials, or combinations thereof. Here, the combined form may include a structure in which one or two or more forms selected from a layer, a rod, a plate, and a wire are regularly or irregularly arranged or laminated to each other. The elements forming the combined form (one or two or more forms selected from a layer, a rod, a plate, and a wire) may be conductive materials of the same kind or different kinds.

The layer may be a dense film (film having no intentional pores), a porous film, or a laminated film thereof. When the first surface is provided by the first conductive member, the upper surface or the lower surface of the layer may correspond to the first surface. Macroscopically, a plate shape may have two opposite surfaces of a polygonal, circular, or oval shape macroscopically and may be in the form having an aspect ratio of 1 or less. When the first surface is provided by the first conductive member, one surface of the two opposite surfaces described above may correspond to the first surface. A wire or rod shape may include a shape in which a cross-sectional area in a major axis is constant or changed continuously or discontinuously. The wire or rod shape has an aspect ratio more than 1, and when a diameter of a cross-section in a minor axis is as small as a cm order ($10^{-2}$ m order) or less, the shape may be regarded as a wire and when a diameter is as large as several cm order or more, the shape may be regarded as a rod. The wire or rod may be a polygonal, circular, or oval shape, and when the first surface is provided by the first conductive member, one end surface or one side of the rod or wire may correspond to the first surface (or a part of the first surface).

In a specific example, the first conductive member and the second conductive member may independently of each other include a network of a one or two or more conductive unit bodies (hereinafter, referred to as a conductive network) selected from mesh; felt; perforated film; fibrous, particulate, tubular, and plate shapes of conductive materials; or combinations thereof. Here, the conductive network may be formed by conductive unit body of one or two or more conductive materials, of course.

Specifically, the conductive network may be a structure in which the conductive unit body of the conductive material described above is physically entangled or physically contacted or bound (including fused) to form a continuous current moving path. A conductive unit body may be a one-dimensional structure having a large aspect ratio such as a fibrous and/or tubular shape, a two-dimensional structure such as a plate shape, and/or a zero-dimensional structure such as a particulate shape, and may include all of two or more structures selected from zero to two-dimensional structures. A fibrous conductive unit body may include any one or two or more selected from conductive carbon fibers, conductive polymer fibers, metal fibers, and the like. A tubular conductive unit body may be a conductive carbon nanotube or a metal tube. Here, the conductive carbon nanotube may be a single walled nanotube, a double walled nanotube, or multiwalled nanotube, and may be a rope nanotube in which a plurality of single walled nanotubes are united, but is not limited thereto. A particulate shape is not particularly limited, but may be conductive carbon particles such as activated carbon, graphite, carbon black, crumpled graphene particles, and rumpled reduced graphene oxide (RGO) particles, or metal particles, conductive polymer particles, or mixed particles thereof, but is not limited thereto. As an example of a plate shape, any one or two selected from graphene and reduced graphene oxide (RGO) which are conductive carbon materials or metal plates may be included, but the present invention is not limited thereto.

In a specific example, the conductive network may be dispersed in and bonded to a non-conductive matrix. That is, the first conductive member and the second conductive member may include a network (conductive network) of one or two or more conductive unit bodies selected from fibrous, particulates, tubular, and plate shapes which are dispersed in and bonded to a non-conductive matrix and a non-conductive matrix. Here, dispersed bonding may be in the form of the conductive network being bound to the surface of the non-conductive matrix or in the form of the conductive network being bound to both the surface and the inside of the non-conductive matrix (in the form of the conductive unit body being dispersed and embedded to be bound to the non-conductive matrix).

Here, the conductive network is bound to both the surface and the inside of the non-conductive matrix and additionally, a second conductive network; a conductive mesh; a conductive perforated film; a shape by a continuous arrangement in which basic units adjoin each other (patterned shape), the basic unit being one or more plate shapes selected from a polygon, a circle, and an ellipse of the conductive materials; a conductive film; a conductive rod; a conductive plate; and/or a conductive wire; and the like may be separately bound to the surface of the non-conductive matrix, of course.

The non-conductive matrix may be porous or non-porous. A non-porous (dense) matrix may mean a matrix in which intentional (or artificial) pores are not formed, and a porous matrix may mean a matrix having an open pore structure. In addition, the non-conductive matrix may have flexibility or stretchability.

As an example of the non-porous non-conductive matrix, the non-conductive matrix may be an insulating resin. The insulating resin may be synthetic resins, natural polymers, biocompatible polymers, or mixtures thereof, and the like, described above. In this case, the first conductive member and the second conductive member may include non-conductive polymer (insulating resin) substrates; and one or two or more conductive unit bodies selected from fibrous, particulate, tubular, and plate shapes which are dispersed and bound to the substrate to form a network. However, in the present invention, the non-conductive matrix is not necessarily limited to resin-based materials, and the non-porous non-conductive matrix does not exclude insulating inorganic materials or insulating organic/inorganic composites. However, the first conductive member and the second conductive member may have improved flexibility and improved adhesion, by the non-conductive matrix of the insulating resin.

Another example of the non-porous non-conductive matrix, the first conductive member and the second conductive member may include non-conductive hydrogel substrates such as collagen, fibrin, hyaluronic acid, polyacrylic acid-based, or polyvinyl alcohol; and one or two or more conductive unit bodies selected from fibrous, particulate, tubular, and plate shapes which are dispersed and bound to the hydrogel substrate to form a network.

As an example of the porous non-conductive matrix, the filament, woven and/or nonwoven form(s) of the non-conductive (insulating) fiber may be included. That is, the porous non-conductive matrix may be in the form of a fiber-based porous web, and the fiber-based porous web may include any one or more selected from filament, woven, and nonwoven forms of fibers, or laminates thereof. Here, the woven form may include a plain woven fabric, a satin woven fabric, a twill woven fabric, a braiding form, a three-dimensional woven form, a contour warp knitting (net-shape weft knitting) form, and the like. In addition, the nonwoven fabric may include felt. Here, the fiber of the porous web may be a natural fiber or a synthetic fiber, but is not limited thereto.

However, the first conductive member or the second conductive member may be the conductive network itself, of course, or the first conductive member or the second conductive member may be a mesh of one or two or more conductive materials selected from conductive carbon materials, conductive polymers, metals, and conductive oxides; a perforated film; a patterned shape by a continuous arrangement in which basic units adjoin each other, the basic unit being one or more plate shapes selected from a polygon, a circle, and an ellipse of the conductive materials, of course. Here, the perforated film may mean a film in which through-type pores through a thickness direction of the film are regularly or irregularly formed. A specific shape of the patterned shape (form) may be a shape corresponding to the stimulation area of the subject to be stimulated, but is not necessarily limited thereto.

As described above, the first conductive member and the second conductive member may be a layer; a rod; a plate; a wire; a foam; a mesh; a perforated film; a patterned shape; a conductive network; a conductive network bound to a non-conductive matrix; of the conductive materials, or composite or laminated structure thereof, but is not necessarily limited thereto.

In addition, when the first conductive member is in the form of an appropriately thin metal film, a mesh, a conductive network, an appropriately thin porous metal film, a conductive network, or a conductive network bound to an insulating resin-based or porous non-conductive matrix, the first conductive member may have high flexibility and belong to a flexible conductive member.

In a specific example, the stimulation apparatus may further include a protective layer which is disposed on a surface of the stimulation part, a surface of the conductive part, or surfaces of the stimulation part and the conductive part exposed to the atmosphere upon contact with the subject to be stimulated through the first surface. Specifically, the protective layer may be configured to cover the surface of the first conductive member, the surface of the second conductive member, or the surfaces of the first conductive member and the second conductive member, when the first conductive member or the first conductive member and/or the second conductive member is/are exposed to the atmosphere. The protective layer may protect the first conductive member or the second conductive member from external moisture or stimulation. As the material of the protective layer, materials which have been conventionally used as a sealing material of a sensor or a semiconductor, such as epoxy-based resins, polyethylene-based resins, polypropylene-based resins, cyclic polyolefin-based resins, polystyrene-based resins, acrylonitrile-styrene copolymers, acrylonitrile-butadiene-styrene copolymers, polyvinyl chloride-based resins, fluorine-based resins, poly(meth)acryl-based resins, and polycarbonate-based resins, are enough.

Figure 6:
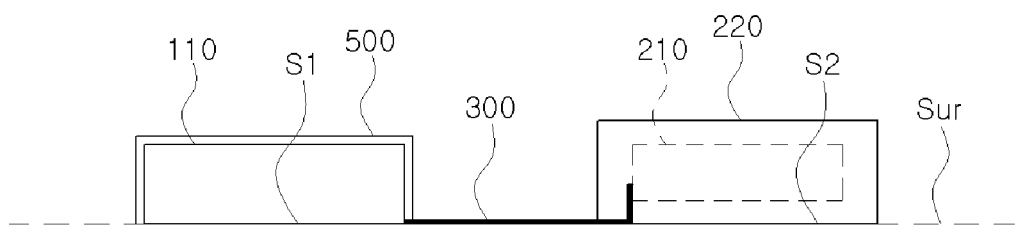
FIG. 6 is a cross-sectional view of the stimulation apparatus according to an exemplary embodiment applied to a subject to be stimulated.

FIG. 6 is an example illustrating a cross-section of the stimulation apparatus applied to the subject to be stimulated, and is a drawing illustrating an example in which the stimulation apparatus further include a protective layer 500. An example of FIG. 6 is an example in which a first surface S1 is provided by a first conductive member 110, and like an example of FIG. 5, the protective layer 500 covers a remaining surface of the first conductive member 110 (an upper surface and a side surface in the drawing).

In a specific example, the stimulation apparatus may include one or more stimulation parts and one or more conductive parts, and a connection member is provided for each stimulation part and one or more stimulation parts may be electrically connected to one or more conductive parts. Specifically, the stimulation apparatus may include N (a natural number of N≥2, substantially 100, 50, or 10 or less) stimulation parts and M (a natural number of 1≤M≤N) conductive parts, and N stimulation parts may be electrically connected to M conductive parts by the connection member provided for each stimulation part. When M is less than N, two or more stimulation parts may be connected to one conductive part, and when M is 1, N stimulation parts may be all connected to a single conductive part. Here, for an electrical connection of N stimulation parts and M conductive parts, which pair N stimulation parts and M conductive parts are connected to does not substantially significantly affect the operation of the apparatus, as long as each stimulation part is connected to the conductive part.

Figure 7:
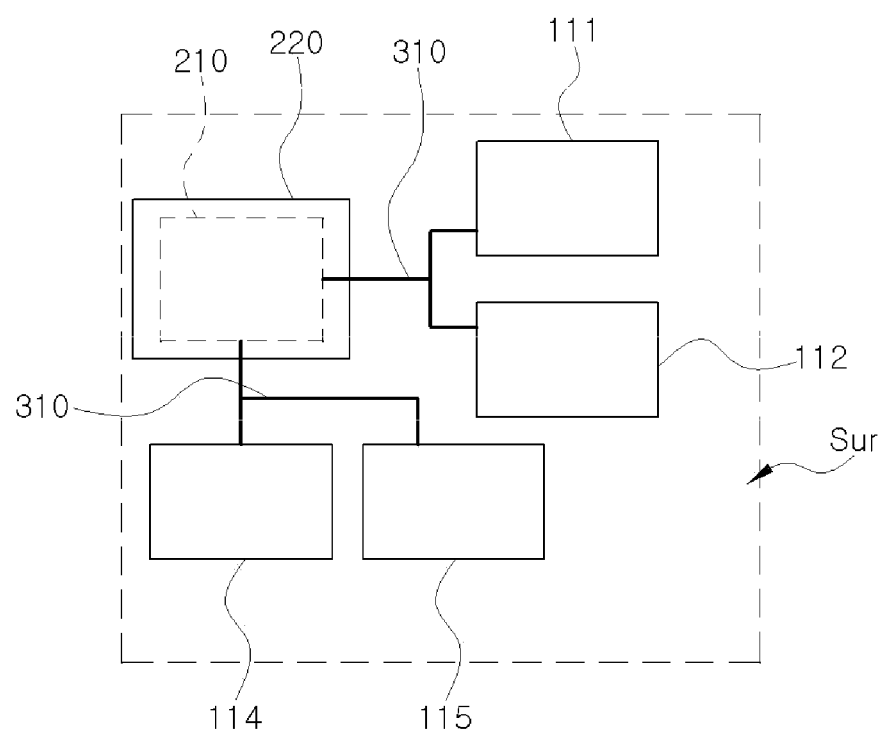
FIG. 7 is a perspective bird's-eye view of the stimulation apparatus including four stimulation parts and one conductive part according to an exemplary embodiment.

FIG. 7 is an example illustrating a stimulation apparatus including four stimulation parts 111-114 and one conductive part 210 and 220. Like FIG. 7, four stimulation parts 111-114 may be electrically connected to a single conductive part 210 and 220 by the connection member 310 provided for each stimulation part 111-114. As in an example illustrated in FIG. 7, a site to which stimulation is applied may be freely changed by adjusting the position or arrangement of N stimulation parts in the subject to be stimulated, upon contact with the subject to be stimulated.

In a specific example, when the stimulation apparatus includes two or more conductive parts, the stimulation apparatus may further include a second connection member electrically connecting two or more conductive parts, specifically second conductive members of the two or more conductive parts to each other. That is, the stimulation apparatus may include N (a natural number of N≥2) stimulation parts and M (a natural number of 2≤M≤N) conductive parts, the N stimulation parts may be electrically connected to the M conductive parts by the connection member provided for each stimulation part, and two or more M conductive parts may be electrically connected to each other by the second connection member connecting the second conductive members of the conductive part from each other.

Figure 8:
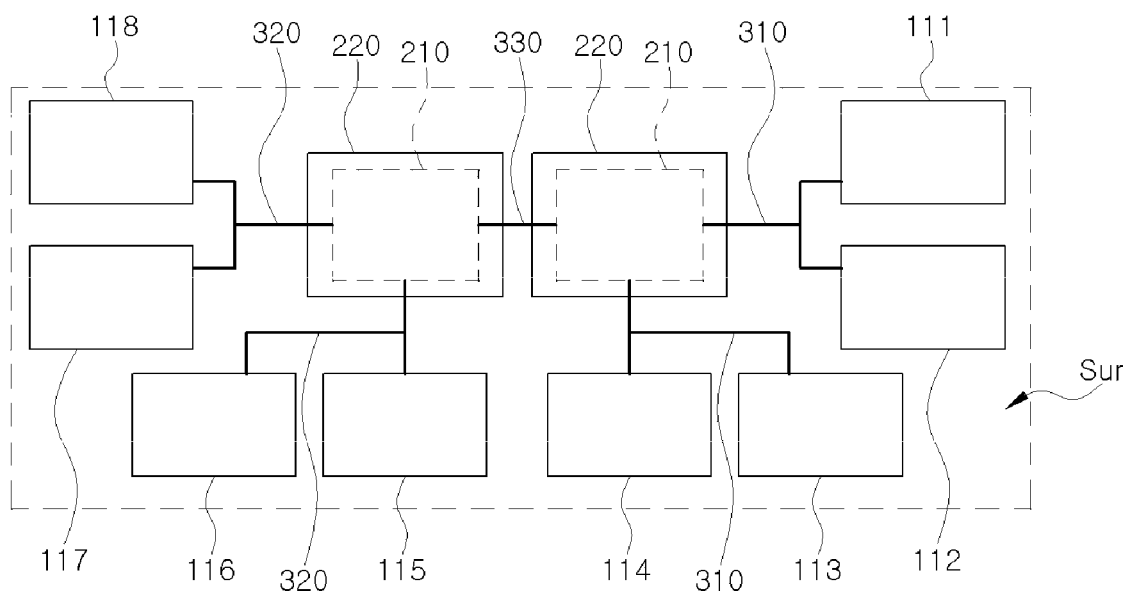
FIG. 8 is a perspective bird's-eye view of the stimulation apparatus including eight stimulation parts and two conductive parts according to an exemplary embodiment.

FIG. 8 is an example illustrating that the stimulation apparatus is provided with two conductive parts 210 and 220, in which the second conductive members 210 of the conductive part are electrically connected to each other by the second connection member 330, and four stimulation parts 111-114 and 115-118 are provided for each conductive part 210 and 220, in which each stimulation part 111-114 and 115-118 is electrically connected to the conductive part 210 and 220 to which the corresponding stimulation part belong by the connection member 320 (first connection member). As in an example illustrated in FIG. 8, upon contact with the subject to be stimulated, stimulation areas far from each other may be stimulated simultaneously with a single stimulation apparatus, only by adjusting the length of the second connection member in the subject to be stimulated.

In a specific example, the entire size and/or shape of the first surface in the stimulation part may correspond to the size and/or shape of the predetermined stimulation area in the subject to be stimulated, but the present invention is not limited thereto.

However, as described above based on the example of FIGS. 7 and 8, when the stimulation apparatus includes two or more stimulation parts, even in the case in which the stimulation part has a smaller size than the size of the predetermined stimulation area, stimulation may be applied to the predetermined stimulation area by the arrangement of the stimulation part, of course.

Figure 9:
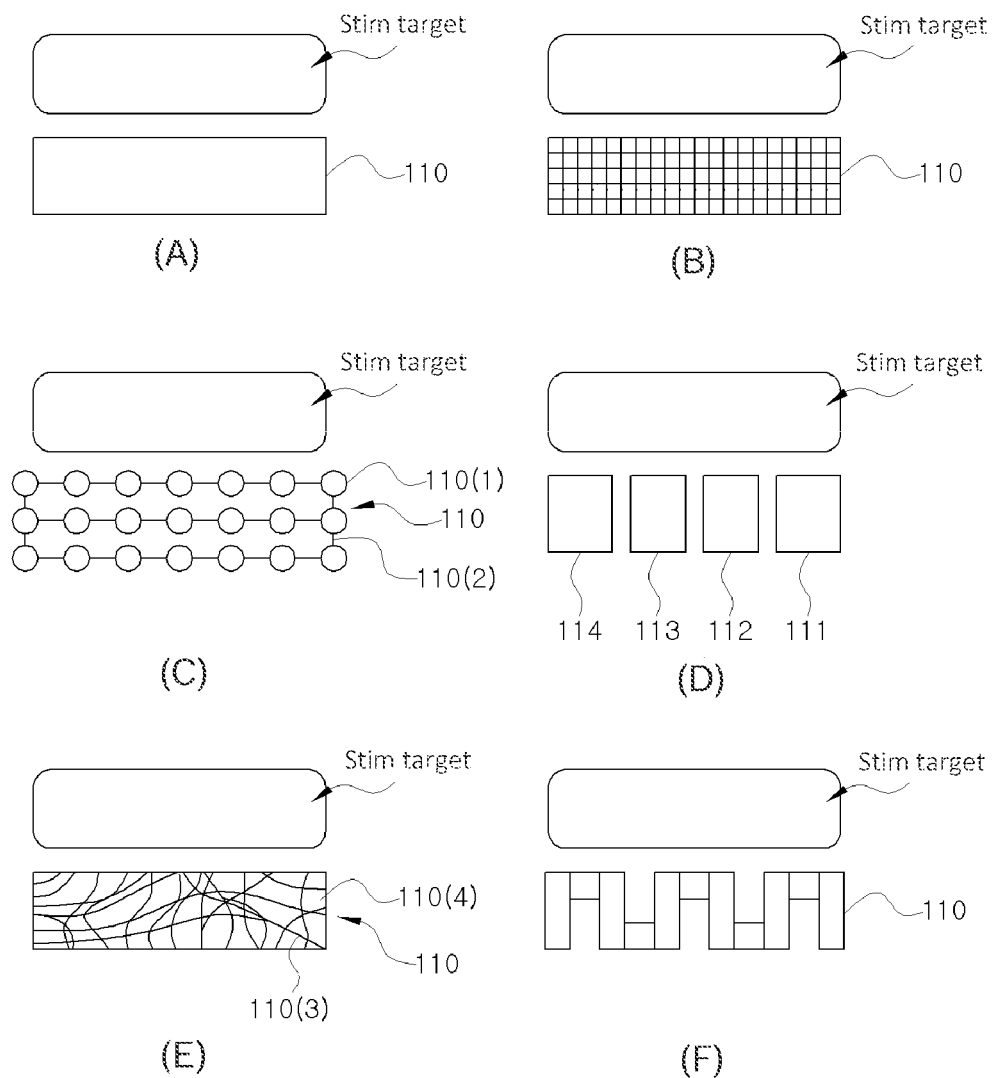
FIG. 9 is a drawing illustrating predetermined stimulation areas (upper portions of (A) to (F) of FIG. 9) and stimulation parts (lower portions of (A) to (F) of FIG. 9) in the apparatus according to an exemplary embodiment, with the subject to be stimulated being a human body.

FIG. 9 is an example illustrating a set of stimulation area-stimulation part of predetermined stimulation areas (upper portions of (A) to (F) of FIG. 9, stim target) and stimulation parts (lower portions of (A) to (F) of FIG. 9) which may apply stimulation to the stimulation area (stim target), a subject to be stimulated being the human body. Specifically, FIG. 9 is a drawing which illustrates various kinds of stimulation parts which may apply stimulation to stimulation areas, and is an example in which the stimulation part is a first conductive member 110 and a first surface is provided by the first conductive member 110.

Specifically, (A) of FIG. 9 is an example illustrating a case in which the first conductive member 110 is a metal film having a shape corresponding to the stimulation area. (B) of FIG. 9 is an example illustrating a case in which the first conductive member 110 is a metal mesh having a shape entirely corresponding to the stimulation area. (C) of FIG. 9 is a drawing illustrating an example in which the first conductive member 110 includes a metal mesh 110 (2) bonded to a metal plate array 110 (1) so that the spherical metal plate array 110 (1) which is regularly arranged to be apart and metal plates are electrically connected to each other. (D) of FIG. 9 is a drawing illustrating an example in which the stimulation apparatus includes four first conductive members 111-114, that is, four stimulation parts, the four first conductive members 111-114 being arranged to cover the stimulation area. (E) of FIG. 9 is a drawing illustrating an example in which the first conductive member 110 includes a network of metal wire 110 (3) and a non-conductive matrix 110 (4) in which metal wires forming the network are dispersed and bonded. (F) of FIG. 9 is an example in which the first conductive member 110 is in a patterned form in which square and rectangular metal plates are continuously bonded to each other, illustrating a form in which the metal plates is arranged in a left and right direction and the upper or lower end of each rectangular metal plate is connected by a square metal plate so that a plurality of metal plates are integrated.

The examples illustrated in FIG. 9 are specific examples of the stimulation part which may cover the stimulation area, and the present invention is not limited to the specific structure or shape of the stimulation part. The stimulation part may be a layer, a rod, a plate, a wire, a foam, a mesh, a perforated film, a patterned shape, a network, or a network bound to a non-conductive matrix of conductive materials, or a structure or a shape in which the forms become a composite or are laminated, or two or more stimulation parts are provided to stably apply stimulation to the predetermined stimulation area.

The stimulation apparatus according to another embodiment is an apparatus applying electrical stimulation to a subject to be stimulated, and includes: a stimulation part including a first conductive member, the first conductive member being configured to be in contact with a subject to be stimulated and including a first surface to which an alternating electric field propagated in the subject to be stimulated is input upon contact; a conductive part including a second connection member and an insulating covering material wrapping the second connection member; and a connection member electrically connecting the first conductive member of the stimulation part and the second conductive member of the conductive part.

As described above, the stimulation apparatus of the present invention does not need artificial electrical energy production equipment or connection with an external power source. However, it should not be construed as excluding apparatuses or components for more increasing triboelectrification which spontaneously occurs in the subject to be stimulated. As an example of the apparatus or components, when the subject to be stimulated is the human body, the stimulation apparatus of the present invention may further include gloves, socks (such as a shoe sole), or the like having a higher electronegativity than the human body.

The present invention includes a stimulation method using the stimulation apparatus described above.

The stimulation method according to the present invention may include: fixing a first surface of the stimulation apparatus to a stimulation area of a subject to be stimulated. That is, the stimulation method may include a step of bringing the first surface of the stimulation part into contact with the stimulation area of the subject to be stimulated to fix the stimulation part to the subject to be stimulated. Here, the fixation may be performed by bringing the first surface into close contact with the subject to be stimulated with a little pressure, and may be performed by a force such as an intermolecular force, a van der Waals force, and/or a London's dispersion force. Unlike this, or in combination therewith, the fixation may be performed by a separate adhesive member such as an adhesive tape.

If necessary, the stimulation method may further include a step of fixing the conductive part to the subject to be stimulated or a separate (other than the subject to be stimulated) member provided in advance in the subject to be stimulated. The fixation of the conductive part may be also performed by bringing the second surface of the conductive part into close contact with the area to which the conductive part is to be fixed (one area of the subject to be stimulated or one area of the separate member provided in advance in the subject to be stimulated) or using the separate adhesive member.

Micro-electrical energy (alternating electric field) is produced by triboelectrification which is inevitable and spontaneously occurs in the subject to be stimulated, and the micro-electrical energy (alternating energy) may be propagated in the subject to be stimulated without a substantial energy loss by a dielectric liquid containing moisture in the subject to be stimulated. When the first surface of the stimulation part is in contact with and fixed to the stimulation area of the subject to be stimulated, the alternating electric field propagated in the subject to be stimulated is input to the stimulation part through the first surface and a potential difference may be generated between the first conductive member and the second conductive member. By the potential difference, an alternating current flows between the first conductive member and the second conductive member and an electrical stimulation may be applied to the stimulation area. Thus, phenomenologically, a method of applying stimulation may include bringing the first surface of the stimulation part into contact with the stimulation area of the subject to be stimulated to fix the stimulation part to the subject to be stimulated; and applying the alternating electric field which is produced by triboelectrification occurring in the subject to be stimulated and propagated in the subject to be stimulated by the dielectric polarization of moisture contained in the subject to be stimulated to the first conductive member through the first surface, forming potentials different from each other in the first conductive member and the second conductive member electrically connected to the first conductive member, producing an alternating current by the different potential, and applying an electrical stimulation to the stimulation area by the alternating current. Thus, as the triboelectrification occurs in the subject to be stimulated more frequently, the frequency of applying an electrical stimulation to the stimulation area may be increased.

As an example in which the subject to be stimulated is the human body, a micro-alternating electric field usually in a level of about 1 to 30 Hz and an order of about $10^{-6}$ to $10^2$ V may be generated by triboelectrification occurring by natural and spontaneous movement of the human body. Thus, as an example in which the subject to be stimulated is the human body, an electrical stimulation at a frequency corresponding to an occurrence frequency of natural occurring triboelectrification, as a substantial example, in a level of 1 to 30 Hz and an order of $\mu V$ to $10^2$ V may be applied to the stimulation area of the human body by the stimulation method according to a specific example. The micro-electrical stimulation having a similar intensity to the bioelectricity is, as is known, effective for wrinkle improvement, promotion of wound and fracture healing, improvement of muscle fatigue, inflammation improvement, blood circulation improvement, abdominal fat reduction, bruise treatment, teeth correction promotion, and the like. The effect may be based on the phenomenon in which cell activity in the living body is promoted by the micro-electrical stimulation.

If necessary, the stimulation method may further include introducing a device or component for increasing triboelectrification which spontaneously occurs in the subject to be stimulated to the area where the triboelectrification occurs in the subject to be stimulated, before, upon, or after fixation of the stimulation part, but the present invention is not limited to whether the device or component is used. Here, an artificial electrical connection between the device or component for increasing triboelectrification in the subject to be stimulated and the device used in the stimulation method (stimulation apparatus) is not necessary, of course.

Hereinabove, although the present invention has been described by specific matters, limited exemplary embodiments, and drawings, they have been provided only for assisting the entire understanding of the present invention, and the present invention is not limited to the exemplary embodiments, and various modifications and changes may be made by those skilled in the art to which the present invention pertains from the description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A stimulation method comprising:
   fixing a first surface of a stimulation apparatus to a stimulation area of a subject to be stimulated; and
   maintaining a constant relative position of a conductive part of the stimulation apparatus to a stimulation part of the stimulation apparatus while the first surface of the stimulation apparatus is being in contact with the subject to be stimulated and an electrical stimulation is being applied to the subject to be stimulated,
wherein the stimulation apparatus comprises:
the stimulation part including a first conductive member and the first surface, the first surface being configured to be in contact with the subject to be stimulated and an alternating electric field propagated in the subject to be stimulated being input to the first surface upon contact;
the conductive part including a second conductive member and being disposed apart from the stimulation part, wherein the conductive part includes a second surface having a higher sheet resistance than a sheet resistance of the first surface; and
a connection member electrically connecting the stimulation part and the conductive part,
wherein the second conductive member of the conductive part is prevented from being in direct contact with the subject to be stimulated.

2. The stimulation method of claim 1, wherein upon the contact, potentials different from each other are formed in the stimulation part and the conductive part by the alternating electric field propagated in the subject to be stimulated.

3. The stimulation method of claim 1, wherein the alternating electric field is caused by triboelectrification.

4. The stimulation method of claim 3, wherein the subject to be stimulated is a living body.

5. The stimulation method of claim 1, wherein upon the contact, the first surface is fixed to the subject to be stimulated, and a contact area between the stimulation part and the subject to be stimulated is maintained constant by the fixation.

6. The stimulation method of claim 1, wherein the conductive part is disposed apart from the stimulation part in a horizontal or vertical direction to the stimulation part.

7. The stimulation method of claim 1, wherein the first surface is provided by a surface of the first conductive member.

8. The stimulation method of claim 1, wherein the second surface is a surface of an insulator.

9. The stimulation method of claim 1, wherein the conductive part is fixed to the subject to be stimulated by the second surface.

10. The stimulation method of claim 1, wherein the second surface is provided by a covering material wrapping the second conductive member.

11. The stimulation method of claim 1, wherein one end of the connection member adjoins the first conductive member and the other end adjoins the second conductive member.

12. The stimulation method of claim 1, wherein the first conductive member and the second conductive member are independently of each other a layer, a rod, a plate, a wire, or a combination thereof.

13. The stimulation method of claim 1, wherein the first conductive member and the second conductive member are independently of each other a mesh; a perforated film; a network of one or two or more conductive unit bodies selected from fibrous, particulate, tubular, and plate shapes; a shape by a continuous arrangement in which basic units adjoin each other, the basic unit being one or more plate shapes selected from a polygon, a circle, and an ellipse of conductive materials; or combinations thereof.

14. The stimulation method of claim 13, wherein the one or two or more conductive unit bodies are dispersed in and bonded to a non-conductive matrix.

15. The stimulation method of claim 1, wherein the first conductive member and the second conductive member are independently of each other metals, conductive carbon materials, conductive organic materials, conductive oxides, or combinations thereof.

* * * * *